US008242089B2

(12) United States Patent
Barenholz et al.

(10) Patent No.: US 8,242,089 B2
(45) Date of Patent: Aug. 14, 2012

(54) SPHINGOLIPIDS POLYALKYLAMINE CONJUGATES FOR USE IN TRANSFECTION

(75) Inventors: Yechezkel Barenholz, Jerusalem (IL); Dmitri Simberg, Jerusalem (IL)

(73) Assignee: Yissum Research Development Company of the Hebrew University of Jerusalem, Jerusalem (IL)

( * ) Notice: Subject to any disclaimer, the term of this patent is extended or adjusted under 35 U.S.C. 154(b) by 1342 days.

(21) Appl. No.: 10/560,932

(22) PCT Filed: Jun. 17, 2004

(86) PCT No.: PCT/IL2004/000533
§ 371 (c)(1),
(2), (4) Date: May 5, 2006

(87) PCT Pub. No.: WO2004/110499
PCT Pub. Date: Dec. 23, 2004

(65) Prior Publication Data
US 2006/0252718 A1 Nov. 9, 2006

Related U.S. Application Data

(60) Provisional application No. 60/479,185, filed on Jun. 18, 2003, provisional application No. 60/505,638, filed on Sep. 25, 2003, provisional application No. 60/537,553, filed on Jan. 21, 2004, provisional application No. 60/545,505, filed on Feb. 19, 2004.

(51) Int. Cl.
*A61K 48/00* (2006.01)
*A61K 9/127* (2006.01)
*C12N 15/00* (2006.01)
*C12N 15/88* (2006.01)

(52) U.S. Cl. ........ 514/44 R; 424/450; 435/455; 435/458

(58) Field of Classification Search .................. None
See application file for complete search history.

(56) References Cited

U.S. PATENT DOCUMENTS

| | | | |
|---|---|---|---|
| 4,897,355 A | 1/1990 | Eppstein et al. | |
| 5,171,678 A | 12/1992 | Behr et al. | |
| 5,334,761 A | 8/1994 | Gebeyehu et al. | |
| 5,659,011 A | 8/1997 | Waldmann | |
| 5,674,908 A | 10/1997 | Haces et al. | |
| 5,783,565 A | 7/1998 | Lee et al. | |
| 5,976,567 A * | 11/1999 | Wheeler et al. | 424/450 |
| 6,075,012 A | 6/2000 | Gebeyehu et al. | |
| 6,117,653 A | 9/2000 | Thoma et al. | |
| 6,281,371 B1 | 8/2001 | Kloesel et al. | |
| 6,300,321 B1 * | 10/2001 | Scherman et al. | 514/44 |
| 7,771,711 B2 | 8/2010 | Barenholz et al. | |
| 2001/0048939 A1 | 12/2001 | Erbacher et al. | |
| 2002/0188023 A1 * | 12/2002 | Jorgensen et al. | 514/552 |
| 2008/0112917 A1 * | 5/2008 | Barenholz et al. | 424/78.27 |

FOREIGN PATENT DOCUMENTS

| | | |
|---|---|---|
| EP | 0 394 111 A1 | 10/1990 |
| JP | 01-213858 | 8/2001 |
| WO | 95/21175 A1 | 8/1995 |
| WO | 97/45442 A1 | 12/1997 |
| WO | WO9745442 A1 * | 12/1997 |
| WO | WO 98/05678 A2 | 2/1998 |
| WO | WO 99/02190 A | 1/1999 |
| WO | 00/37046 A1 | 6/2000 |
| WO | 01/38295 A1 | 5/2001 |
| WO | 01/48233 A1 | 7/2001 |
| WO | WO 03/066068 A1 | 8/2003 |
| WO | 2004/110496 A1 | 12/2004 |
| WO | 2004/110499 A1 | 12/2004 |
| WO | 2004/110980 A1 | 12/2004 |

OTHER PUBLICATIONS

Cabral et al., "Cellular and Humoral Immunity in Guinea Pigs to Two Major Polypeptides Derived from Hepatitis B Surface Antigen" J. gen. Virol. 38, 339-350 (1978).
Diminsky et al., "Structural and Functional Characterization of Liposomal Recombinant Hepatitis B Vaccine" Journal of Liposome Research 6(2), 289-304 (1996).
Diminsky et al., "Comparison between hepatitis B surface antigen (HBsAg) particles derived from mammalian cells (CHO) and yeast cells (Hansen&a polymorpha): composition, structure and immunogenicity" Vaccine, vol. 15, No. 6/7, pp. 637-647 (1997).
Gavilanes et al., "Hepatitis B surface antigen—Role of lipids in maintaining the structural and antigenic properties of protein components" Biochem. J. 265, 857-864 (1990).
Gomez-Gutierrez et al., "Reconstitution of hepatitis B surface antigen proteins into phospholipid vesicles" Biochimica et Biophysica Acta 1192: 45-52 (1994).
Hermanson., "Bioconjugate Techniques" Academic Press, San Diego, CA, pp. 154-155 (1996). Valenzuela et al., "Synthesis and assembly of hepatitis B virus surface antigen particles in yeast" Nature, 298:22 (1982).
International Search Report mailed Oct. 22, 2004 (corresponding PCT Appln. No. PCT/IL2004/000533).
International Search Report mailed Nov. 16, 2004 (corresponding PCT Appln. No. PCT/IL2004/000534).
International Search Report mailed Oct. 22, 2004 (corresponding PCT Appln. No. PCT/IL2004/000536).
Australian Patent Office Examination Report mailed Jun. 30, 2006 (corresponding Singapore Application No. SG200508078-3).
F. Brunel et al., "Cationic lipid DC-Chol induces an improved and balanced immunity able to overcome the unresponsiveness to the hepatitis B vaccine", *Vaccine* vol. 17, pp. 2192-2203, 1999.
K. Ewert et al., "Efficient Synthesis and Cell-Transfection Properties of a New Multivalent Cationic Lipid for Nonviral Gene Delivery", *J. Med. Chem.* vol. 45, pp. 5023-5029, 2002.

(Continued)

*Primary Examiner* — Janet Epps-Smith
(74) *Attorney, Agent, or Firm* — Browdy and Neimark, PLLC

(57) ABSTRACT

The present invention concerns the use of a sphingoid-polyalkylamine conjugate comprising a sphingoid backbone carrying, via a carbamoyl bond, at least one polyalkylamine chains as a capturing agent of nucleic acid molecules. The present invention also provides the use of the sphingoid polyalkylamine conjugate for the preparation of a pharmaceutical composition for the delivery of a nucleic acid molecule into a target cell. In a further aspect the invention provides a method for transfecting a nucleic acid into a target cell, the method comprises contacting said target cell with the sphingoid-polyalkylamine conjugate associated with a nucleic acid molecule, thereby transfecting said target cell with said nucleic acid molecule. Other aspects of the invention concern pharmaceutical compositions comprising said conjugate, therapeutic methods as well as kits, making use of the said conjugate. A preferred conjugate according to the invention is N-palmitoyl D-erythrosphingosyl-1-carbamoyl spermine.

20 Claims, 8 Drawing Sheets

OTHER PUBLICATIONS

P. L. Felgner et al., "Lipofection: A highly efficient, lipid-mediated DNA-transfection procedure", *Proc. Natl. Acad. Sci. USA.*, vol. 84, pp. 7413-7417, Nov. 1987.

X. Gao et al., "A Novel Cationic Liposome Reagent or Efficient Transfection of Mammalian Cells", *Biochim. Acta.* vol. 179, pp. 280-285, 1999.

B. Guy et al., "Design, characterization and preclinical efficacy of a cationic lipid adjuvant for influenza split vaccine", *Vaccine*, vol. 19, pp. 1794-1805, 2001.

M. A. Ilies et al., "Recent developments in cationic lipid-mediated gene delivery and gene therapy", *Expert.Opin. Ther. Patents.*, vol. 11, No. 11, pp. 1729-1752, 2001.

K. M. Lima et al., "Comparison of different delivery systems of vaccination for the induction of protection against tuberculosis in mice", *Vaccine*, vol. 19, pp. 3518-3525, 2001.

A. D. Miller, "Cationic Liposomes for Gene Therapy", *Chem. Int. Ed. Eng.*, vol. 37, pp. 1768-1785, 1987.

T. Nakanishi et al., "Positively charged liposome functions as an efficient immunoadjuvant in inducing cell-mediated immune response to soluble proteins", *J. Controlled Release*, vol. 61, pp. 233-240, 1999.

M. Saminathan et al., "Ionic and Structural Specificity Effects of Natural and Synthetic Polyamines on the Aggregation and Resolubilization of Single-, Double-, and Triple-stranded DNA", *Biochemistry*, vol. 38, pp. 3821-3830, 1999.

U.S. Appl. No. 10/560,928, filed Jun. 17, 2004.

Official Action dated Oct. 27, 2009, in U.S. Appl. No. 10/560,928.

Final Official Action dated May 26, 2010, in U.S. Appl. No. 10/560,928.

U.S. Appl. No. 11/345,624, filed Feb. 2, 2006.

Li, S. et al. "Nonviral gene therapy: promises and challenges" Gene Ther, 7(1): p. 31-4. (2000).

Chesnoy, S. et al., "Structure and function of lipid-DNA complexes for gene delivery" Annu Rev Biophys Biomol Struct, 29: p. 27-47 (2000).

Harrington, J.J., et al., "Formation of de novo centromeres and construction of first-generation human artificial microchromosomes" Nat Genet, 15(4): p. 345-55. (1997).

Willard, H.F., "Genomics and gene therapy Artificial chromosomes coming to life" Science, 290(5495): p. 1308-9 (2000).

Felgner, P.L., et al., "Lipofection: a highly efficient, lipid-mediated DNA-transfection procedure" Proc Natl Acad Sci U S A, 84(21): p. 7413-7 (1987).

Boussif, O., et al., "A versatile vector for gene and oligonucleotide transfer into cells in culture and in vivo: polyethylenimine" Proc Natl Acad Sci U S A, 92(16): p. 7297-301 (1995).

Kerner, M., et al., "Interplay in lipoplexes between type of pDNA promoter and lipid composition determines transfection efficiency of human growth hormone in NIH3T3 cells in culture" Biochim Biophys Acta,1532(1-2): p. 128-36. (2001).

Zuidam, N.J. and Y. Barenholz., "Electrostatic parameters of cationic liposomes commonly used for gene delivery as determined by 4-heptadecyl-7-hydroxycoumarin" Biochim Biophys Acta, 1329(2): p. 211-22. (1997).

Zuidam, N.J. and Y. Barenholz., "Electrostatic and structural properties of complexes involving plasmid DNA and cationic lipids commonly used for gene delivery" Biochim Biophys Acta, 1368(1): p. 115-28. (1998).

Lam, A.M. and P.R. Cullis., "Calcium enhances the transfection potency of plasmid DNA-cationic liposome complexes" Biochim Biophys Acta, 1463(2): p. 279-90. (2000).

Bailey, A.L. and S.M. Sullivan., "Efficient encapsulation of DNA plasmids in small neutral liposomes induced by ethanol and calcium" Biochim Biophys Acta, 1468(1-2): p. 239-52 (2000).

* cited by examiner

SEQUENCE LISTING

<160> NUMBER OF SEQ ID NOS: 1

<210> SEQ ID NO 1
<211> LENGTH: 18
<212> TYPE: DNA
<213> ORGANISM: Artificial Sequence
<220> FEATURE:
<223> OTHER INFORMATION: synthetic

<400> SEQUENCE: 1
tctcccagcg tgcgccat                                            18

SPHINGOLIPIDS POLYALKYLAMINE CONJUGATES FOR USE IN TRANSFECTION

FIELD OF THE INVENTION

The present invention concerns the use of sphingolipids' polyalkylamines conjugates as delivery vehicles, for effective transfection of biologically active agents, particularly poly- and oligo nucleotides into target cells.

LIST OF PRIOR ART

The following is a list of prior art which is considered to be pertinent for describing the state of the art in the field of the invention.
U.S. Pat. No. 5,334,761: "Cationic lipids";
US 2001/048939: "Cationic reagents of transfection";
U.S. Pat. No. 5,659,011: "Agents having high nitrogen content and high cationic charge based on dicyanimide dicyandiamide or guanidine and inorganic ammonium salts";
U.S. Pat. No. 5,674,908: "Highly packed polycationic ammonium, sulfonium and phosphonium lipids";
U.S. Pat. No. 6,281,371: "Lipopolyamines, and the preparation and use thereof";
U.S. Pat. No. 6,075,012: "Reagents for intracellular delivery of macromolecules";
U.S. Pat. No. 5,783,565: "Cationic amphiphiles containing spermine or spermidine cationic Marc Antoniu Ilies & Alexandru T. Balaban, Expert Opin. Ther. Patents. 11(11): 1729-1752 (2001);
Miller A D. Chem. Int. Ed. Eng. 37:1768-1785 (1998).
Gao X, Huang L. "A novel cationic liposome reagent for efficient transfection of mammalian cells" Biochim. Biophys. Acta 179: 280-285 (1999).
Max-Delbruck-Centrum fur Molekulare Medizine: WO 98/05,678 (1998).
Miller A D "Cationic liposomes for gene therapy" Angew. Chem. Int. Ed. Eng. 37:1768-178 (1998).
Ewert K. et. al. "Efficient synthesis and cell-transfection properties of a new multivalent cationic lipid for nonviral gene delivery". J Med Chem. 45:5023-5029 (2000).

BACKGROUND OF THE INVENTION

Many natural biological molecules and their analogues, including proteins and polynucleotides, foreign substances and drugs, which are capable of influencing cell function at the sub-cellular or molecular level are preferably incorporated within the cell in order to produce their effect. For these agents the cell membrane presents a selective barrier which is impermeable to them. The complex composition of the cell membrane comprises phospholipids, glycolipids, and cholesterol, as well as intrinsic and extrinsic proteins, and its functions are influenced by cytoplasmic components which include $Ca^{++}$ and other metal ions, anions, A, microfilaments, microtubules, enzymes, and $Ca^{++}$-binding proteins, also by the extracellular glycocalyx (proteoglycans, glycose aminoglycans and glycoproteins). Interactions among structural and cytoplasmic cell components and their response to external signals make up transport processes responsible for the membrane selectivity exhibited within and among cell types.

Successful delivery of agents not naturally taken up by cells into cells has also been investigated. The membrane barrier can be overcome by associating agents in complexes with lipid formulations closely resembling the lipid composition of natural cell membranes. These formulations may fuse with the cell membranes on contact, or what is more common, taken up by pynocytosis, endocytosis and/or phagocytosis. In all these processes, the associated substances are delivered in to the cells.

Lipid complexes can facilitate intracellular transfers also by overcoming charge repulsions between the cell surface, which in most cases is negatively charged. The lipids of the formulations comprise an amphipathic lipid, such as the phospholipids of cell membranes, and form various layers or aggregates such as micelles or hollow lipid vesicles (liposomes), in aqueous systems. The liposomes can be used to entrap the substance to be delivered within the liposomes; in other applications, the drug molecule of interest can be incorporated into the lipid vesicle as an intrinsic membrane component, rather than entrapped into the hollow aqueous interior, or electrostatically attached to aggregate surface. However, most phospholipids used are either zwiterionic (neutral) or negatively charged.

An advance in the area of intracellular delivery was the discovery that a positively charged synthetic cationic lipid, N-[1-(2,3-dioleyloxy)propyl]-N,N,N-trimethylammonium chloride (DOTMA), in the form of liposomes, or small vesicles, could interact spontaneously with DNA to form lipid-DNA complexes which are capable of adsorbing to cell membranes and being taken up by the cells either by fusion or more probably by adsorptive endocytosis, resulting in expression of the transgene [Felgner, P. L. et al. Proc. Natl. Acad. Sci., USA 84:7413-7417 (1987) and U.S. Pat. No. 4,897,355 to Eppstein, D. et al.]. Others have successfully used a DOTMA analogue, 1,2-bis(oleoyloxy)-3-(trimethylammonio)propane (DOTAP) in combination with a phospholipid to form DNA-complexing vesicles. The Lipofectin™ reagent (Bethesda Research Laboratories, Gaithersburg, Md.), an effective agent for the delivery of highly anionic polynucleotides into living tissue culture cells, comprises positively charged liposomes composed of positively charged lipid DOTMA and a neutral lipid dioleyl phosphatidyl ethanol amine (DOPE) referred to as helper lipids. these liposomes interactspontaneously with negatively charged nucleic acids to form complexes, referred to as lipoplexes. When excess of positively charged liposomes over DNA negative charges are used, the net charge on the resulting complexes is also positive. Positively charged complexes prepared in this way spontaneously attach to negatively charged cell surfaces or introduced into the cells either by adsorptive endocytosis or fuse with the plasma membrane, both processes deliver functional polynucleotide into, for example, tissue culture cells. DOTMA and DOTAP are good examples for monocationic lipids. [Illis et al. 2001, ibid.]

Multivalent cations by themselves (including polyamines, inorganic salts and complexes and dehydrating solvents) have also been shown to facilitate delivery of macromolecules into cells. In particular, multivalent cations provoke the collapse of oligo and polyanions (nucleic acids molecules, amino acid molecules and the like) to compact structural forms, and facilitate the packaging of these polyanions into viruses, their incorporation into liposomes, transfer into cells etc. [Thomas T. J. et al. Biochemistry 38:3821-3830 (1999)]. The smallest natural polycations able to compact DNA are the polyamines spermidine and spermine. By attaching a hydrophobic anchor to these molecules via a linker, a new class of transfection vectors, the polycationic lipopolymers, has been developed.

Cationic lipids and cationic polymers interact electrostatically with the anionic groups of DNA (or of any other polyanionic macromolecule) forming DNA-lipid complexes (lipoplexes) or DNA-polycation complexes (polyplexes). The formation of the complex is associated with the release of counterions of the lipids or polymer, which is the thermodynamic driving force for lipoplex and polyplex spontaneous formation. The cationic lipids can be divided into four classes: (i) quaternary ammonium salt lipids (e.g. DOTMA (Lipofectin™) and DOTAP) and phosphonium/arsonium congeners; (ii) lipopolyamines; (iii) cationic lipids bearing both quaternary ammonium and polyamine moieties and (iv) amidinium, guanidinium and heterocyclic salt lipids.

SUMMARY OF THE INVENTION

According to a first of its aspects, the present invention provides the use of a sphingoid-polyalkylamine conjugate for the preparation of a pharmaceutical composition for the transfection of a nucleic acid molecule into a target cell, wherein said sphingoid-polyalkylamine conjugate comprises a sphingoid backbone carrying, via a carbamoyl bond, at least one polyalkylamine chains.

The term "transfection" as used herein denotes the introduction of a nucleic acid molecule into a target cell in a productive manner, namely, which results in transgene expression (for genes (DNA) delivery) or in gene silencing (siRNA or antisense oligonucleotides (ODN) delivery). The nucleic acid molecule may be maintained in the cytoplasm, e.g. in case of delivery of siRNA or antisense ODN, or further delivered into the nucleus (in the case of gene delivery) to act either episomaly or to be subsequent integrated into the cell's chromosomal DNA.

The "target cell" as used herein preferably denotes a tissue an organ or a bone, although may be any biological cell.

The term sphingoid-polyalkylamine conjugate as used herein denotes chemical conjugation (linkage) between a sphingoid base (herein also referred to by the term "sphingoid backbone") and at least one polyalkylamine chain. The conjugation between the sphingoid base and the at least one polyalkylamine chain is via a carbamoyl bond, as further detailed hereinafter.

The sphingoid base/backbone, as used herein, includes, long chain aliphatic amines, containing two or three hydroxyl groups, the aliphatic chain may be saturated or unsaturated. One example of an unsaturated sphingoid base is that containing a distinctive trans-double bond in position 4.

According to one particular embodiment, the sphingoid-polyalkylamine conjugate is N-palmitoyl D-erythro sphingosyl carbamoyl-spermine (CCS).

The present invention also provides a method for transfecting a nucleic acid into a target cell, said method comprises contacting said target cell with a sphingoid-polyalkylamine conjugate together with a nucleic acid molecule, wherein said sphingoid-polyalkylamine conjugate comprises a sphingoid backbone caring, via a carbamoyl bond, at least one polyalkylamine, and thereby transfecting said target cell with the nucleic acid molecule.

The present invention further provides a pharmaceutical composition for transfecting a nucleic acid into a target cell, the composition comprises: (i) at least one sphingoid-polyalkylamine conjugate, said sphingoid-polyalkylamine conjugate comprises a sphingoid backbone carrying, via a carbamoyl bond, at least one polyalkylamine chains; and (ii) at least one nucleic acid molecule associated with said conjugate.

Yet further, the present invention provides a method for the treatment of a disease or disorder, the method comprises providing a subject in need of said treatment an amount of a sphingoid-polyalkylamine conjugate together with a nucleic acid molecule, the amount being effective to achieve transfection of a target cell with said nucleic acid molecule to achieve thereby a biochemical effect on said target cell.

Finally, the invention provides the use of a sphingoid-polyalkylamine conjugate as defined as a capturing agent of nucleic acid molecules (genes, siRNA, antisense, etc.). In this context, the sphingoid-polyalkylamine conjugate may form part of a kit comprising, in addition to said conjugate instructions for use of same for capturing nucleic acid molecules. The conjugate in the kit may be in a dry form, in which case, the kit may also include a suitable fluid with which the conjugate is mixed prior to use, or in a fluid form, in order to form a suspension, emulsion or solution. The kit may have numerous applications. For example, the kit may be used for investigating the function of different nucleic acid molecules. Those versed in the art will know how to make use of such a capturing agent also for research and diagnostic purposes.

The term capturing agent as used herein refers to the characteristics of the conjugate of the invention to interact with molecules having a negative charge, a negative dipole or a local negative dipole. By said interaction, the conjugate of the invention may be applicable in research which involves, e.g. the identification and isolation, by capturing, of, e.g. biologically active molecules such as nucleic acid molecules, for example, from an unknown biological sample. The capturing involves electrostatic interaction between the molecule to be captured, carrying a negative charge, a negative dipole or a local negative charge and the positively charged conjugate of the invention.

The conjugate of the invention may also be used as a delivery vehicle, carrying, by capturing, biologically active molecules as defined above to a target site/into a target cell.

BRIEF DESCRIPTION OF THE FIGURES

In order to understand the invention and to see how it may be carried out in practice, some embodiments will now be described, by way of non-limiting examples only, with reference to the accompanying figures, in which:

FIG. 1A-1D show several possible chemical structures, "linear", branched" or "cyclic" which are encompass under the general definition of sphingoid-polyalkylamine conjugate of formula (I), wherein FIG. 1A shows a sphingoid backbone (ceramide) linked to a single polyalkylamine chain, FIGS. 1B and 1C show the same sphingoid backbone linked to two polyalkylamine chains, FIG. 1D shows again the same backbone, however, in which a single polyalkylamine chain is linked via the two hydroxyl moieties to form a cyclic polyalkylamine conjugate.

DETAILED DESCRIPTION OF THE INVENTION

Figures 1A, 1B:
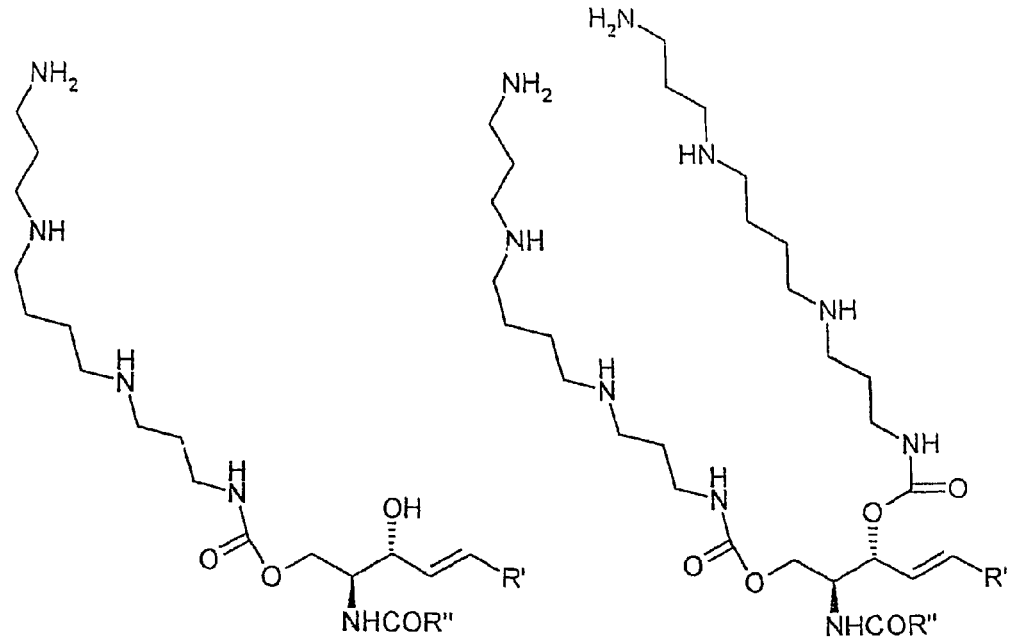

In recent years non-viral delivery of genes into cells using cationic lipid/liposome has emerged as the method of choice because of its high transfection efficiency, ease of use, and reproducibility. In addition, liposomes are synthetic, noninfectious particles which by themselves do not initiate an adverse toxic or immune reaction. Consequently, cationic lipids have been developed that are capable of forming complexes with nucleic acids through electrostatic interactions, overcoming earlier gene size limitations. The resultant liposome-DNA complex is termed a lipoplex.

The present invention concerns the use of sphingoid-polyalkylamine conjugates for the preparation of a pharmaceutical composition for delivering/transfecting into a target cell a nucleic acid molecule, wherein said sphingoid-polyalkylamine conjugate comprises a sphingoid backbone carrying, via a carbamoyl bond, at least one, preferably, one or two, polyalkylamine chains.

The sphingoid-polyalkylamine conjugates are lipid-like cationic (LLC) compounds, which may be synthesized in the following manner. N-substituted long-chain bases in particular, N-substituted sphingoids or sphingoid bases are coupled together with different polyalkylamines or their derivatives, to form a polyalkylamine-sphingoid entity, which is used as is, or further alkylated. Protonation at a suitable pH or alkylation of the formed polyalkylamine-sphingoid entity attributes to the lipid-like compounds a desired positive charge for interaction with biologically active biological molecules to be delivered into target cells and with the targeted cells. The sphingoid-polyalkylamine conjugates, may be efficiently associated with the biologically active molecules by virtue of electrostatic interactions between the anionic character of the biologically active molecules and the polyalkylamine moieties of the conjugate to form complexes (lipoplexes).

Alternatively, the sphingoid-polyalkylamine conjugates may form assemblies loaded or associated with the biologically active molecules. When the assemblies are in the form of vesicles (e.g. liposomes) the biologically active molecule may be encapsulated within the vesicle, part of its lipid bilayer, or adsorbed to the surface of the vesicle (or any combination of these three options). When the assemblies are micelles, the biologically active molecules may be inserted into the amphiphiles forming the micelles and/or associated with it electrostatically, in a stable way.

Thus, as used herein below, the terms "encapsulated in", "contained in", "loaded onto" or "associated with" indicate a physical attachment/association between the conjugate and the biologically active molecule. The physical attachment may be either containment or entrapment of the molecule within assemblies (e.g. vesicles) formed from the conjugate; non-covalent linkage of the biological molecule to the surface such assemblies, or embedment of the biological molecule in between the sphingoid-polyalkylamine conjugates forming such assemblies (vesicles, micelles or other assemblies). The interaction may also include adsorption to the surface of the assembly. It should be noted that due to the positive charge of the sphingoid-polyalkylamine conjugate under physiological conditions, the preferred association between the conjugate and the biologically active molecule is by electrostatic, dipole, acid-base and/or by hydrophobic interactions, or any combination of these interactions.

The term "nucleic acid molecule" as used herein refers to an oligomer or polymer containing at least two nucleotides. Preferably, the nucleic acid molecule has, under physiological pH, a net negative charge, a local negative charge, or a net negative dipole.

The term "nucleotide" is used to denote a sugar deoxyribose (DNA) or ribose (RNA), a base, and a phosphate group. Nucleotides are linked together through a phosphate group. Nucleotides are the monomeric units of a nucleic acid polymer or oligomer.

When in association with nucleotides, the term "base" denotes purines and pyrimidines, which further include natural compounds adenine, thymine, guanine, cytosine, uracil, inosine, and natural analogs, and synthetic derivatives of purines and pyrimidines, which include, but are not limited to, modifications which place new reactive groups such as, but not limited to, amines, alcohols, thiols, carboxylates, and alkyllialides. Nucleotides are the monomeric units of nucleic acid polymers.

The term "polynucleotide" is distinguished herein from an "oligonucleotide" by containing more than 80 monomeric units; oligonucleotides contain from 2 to 80 nucleotides. The term nucleic acid includes deoxyribonucleic acid (DNA) and ribonucleic acid (RNA). The term encompasses sequences that include any of the known base analogs of DNA and RNA.

In addition, DNA may be in the form of anti-sense, oligonucleotide plasmid DNA, parts of a plasmid DNA, product of a polymerase chain reaction (PCR), vectors (PI, PAC, BAC, YAC, artificial chromosomes), expression cassettes, chimeric sequences, chromosomal DNA, or derivatives of these groups. RNA may be in the form of oligonucleotide RNA, tRNA (transfer RNA), snRNA (small nuclear RNA), siRNA (small interference RNA) rRNA (ribosomal RNA), mRNA (messenger RNA), anti-sense RNA, ribozymes, chimeric sequences, or derivatives of these groups. In this connection, the term "antisense" is used to denote a nucleic acid molecule (poly or oligo) that interferes with the function of DNA and/or RNA. This may result in suppression of expression.

Natural nucleic acids have a phosphate backbone; artificial nucleic acids may contain other types of backbones and bases. These include PNAs (peptide nucleic acids), phosphothionates, and other variants of the phosphate backbone of native nucleic acids.

In addition, DNA and RNA may be single, double, triple, or quadruple stranded.

According to one embodiment, the nucleic acid molecule is selected from oligodeoxynucleotide (ODN), more specifically, ODN containing at least one CpG motif (CpG-ODN); a small interfering RNA (siRNA), for example, anti-Bcl-2 siRNA; plasmid DNA; and antisense RNA or antisense DNA.

The target cells according to the invention include a cell per se or a component thereof (e.g. intracellular component), a tissue, an organ or a bone.

The sphingoid-polyalkylamine conjugate includes a linkage between a sphingoid backbone and at least one polyalkylamine chain, the linkage is via corresponding carbamoyl bonds. More preferably, the sphingoid-polyalkylamine conjugate has the general formula (I):

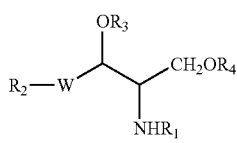

wherein

R$_1$ represents a hydrogen, a branched or linear alkyl, aryl, alkylamine, or a group —C(O)R$_5$;

R$_2$ and R$_5$ represent, independently, a branched or linear C$_{10}$—C$_{24}$ alkyl, alkenyl or polyenyl groups;

R$_3$ and R$_4$ are independently a group —C(O)—NR$_6$R$_7$,

R$_6$ and R$_7$ being the same or different for R$_3$ and R$_4$ and represent, independently, a hydrogen, or a saturated or unsaturated branched or linear polyalkylamine, wherein one or more amine units in said polyalkylamine may be a quaternary ammonium;

or R$_3$ is a hydrogen;

or R$_3$ and R$_4$ form together with the oxygen atoms to which they are bound a heterocyclic ring comprising —C(O)—NR$_9$—[R$_8$—NR$_9$]$_m$—C(O)—, R$_8$ represents a saturated or unsaturated C$_1$-C$_4$ alkyl and R$_9$ represents a hydrogen or a polyalkylamine of the formula —[R$_8$—NR$_9$]$_n$—, wherein said R$_9$ or each alkylamine unit R$_8$NR$_9$ may be the same or different in said polyalkylamine; and n and m represent independently an integer from 1 to 10 and preferably from 3 to 6;

W represents a group selected from —CH=CH—, —CH$_2$—CH(OH)— or —CH$_2$—CH$_2$—;

including stereoisomers and salts of the above compound.

Preferably, according to this specific embodiment, the sphingoid-polyalkylamine conjugate is such that R$_1$ represents a —C(O)R$_5$ group, R$_5$ being as defined, R$_2$ and R$_5$ represent, independently, a linear or branched C$_{12}$-C$_{18}$ alkyl or alkenyl groups, W represents —CH=CH—.

Non-limiting examples of the sphingoids or sphingoid bases which may be used according to a more specific embodiment of the invention, include, sphingosines, dihydrosphingosines, phytosphingosines, dehydrophytosphinosine, as well as ceramines (N-alkylsphinogsine) and the corresponding derivatives (e.g. dihydroceramine, phytoceramine etc.) of any chain length in the range of 12-26 carbon atoms and derivatives thereof. Non-limiting examples of such derivatives are acyl derivatives, such as ceramide (N-acylsphingosine), dihydroceramides, phytoceramides and dihydrophytoceramides, respectively. The suitably N-substituted sphingoids or sphingoid bases posses free hydroxyl groups which are activated and subsequently reacted with the polyalkylamines to form the polyalkylamine-sphingoid entity. Non-limiting examples of activation agents are N,N'-disuccinimidylcarbonate, di- or tri-phosgene or imidazole derivatives. The reaction of these activation agents with the sphingoids or the sphingoid bases yields a succinimidyloxycarbonyl, chloroformate or imidazole carbamate, respectively, at one or both hydroxyls. The reaction of the activated sphingoids with polyalkylamines may yield branched, straight (unbranched) or cyclic conjugates as shown in FIGS. 1A-1D. A preferred sphingoid backbone is ceramide.

A preferred group of polyalkylamine chains forming part of the sphingoid-polyalkylamine conjugate have been structurally defined hereinabove in connection with formula (I). More preferably, the polyalkylamine chains, which may be the same or different in the same conjugate, are selected from spermine, spermidine, a polyalkylamine analog or a combination of same thereof.

The term polyalkylamine analog is used to denote any polyalkylamine chain, and according to one embodiment denotes a polyalkylamine comprising 1 to 10 amine groups, preferably 3 or 6 amine groups and more preferably 3-4 amine groups. Each alkylamine within the polyalkylamine chain may be the same or different and may be a primary, secondary, tertiary or quaternary amine.

The alkyl moiety, which may be the same or different within the polyalkylamine chain, is preferably a C$_1$-C$_6$ aliphatic repeating unit and more preferably C$_3$-C$_6$ aliphatic repeating unit. Some non-limiting examples of polyalkylamins include spermidine, N-(2-aminoethyl)-1,3-propanediamine, 3,3'-iminobispropylamine, spermine and bis(ethyl) derivatives of spermine, polyethyleneimine.

A preferred polyalkylamine chain according to the invention is spermine.

Figures 1C, 1D:
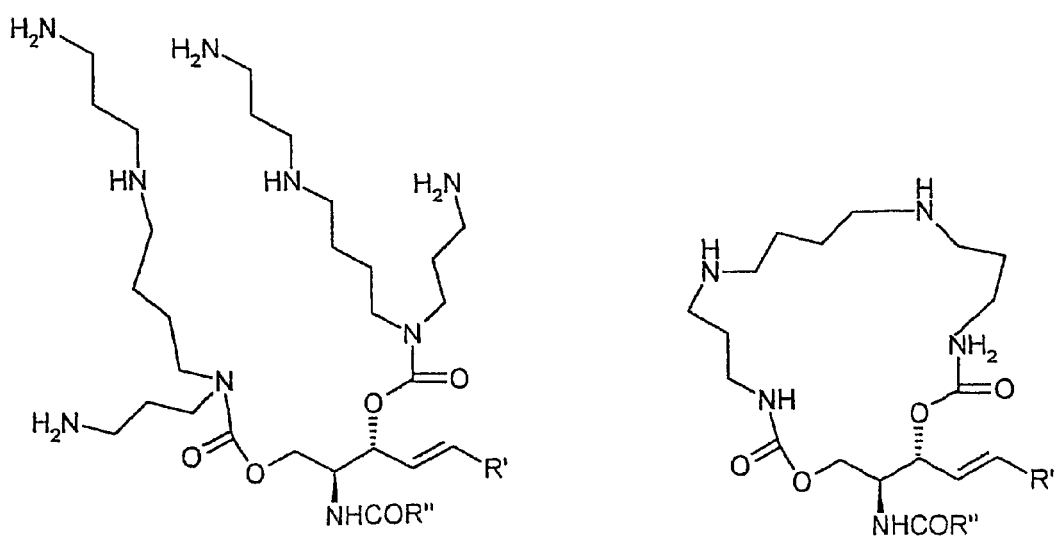

According to one preferred embodiment the sphingoid backbone is a ceramide linked to one (e.g. as depicted in FIG. 1A) or two (e.g. as depicted in FIG. 1B or 1C) polyalkylamine chains, or linked via the two hydroxyl moieties to form a cyclic polyalkylamine moiety (e.g. as depicted in FIG. 1D).

The most preferred sphingoid-polyalkylamine conjugate according to the invention is N-palmitoyl D-erythro sphingosyl carbamoyl-spermine (CCS). This conjugate includes a ceramide linked via a carbamoyl bond to spermine.

The formed sphingoid-polyalkylamine conjugates may be further reacted with methylation agents in order to form quaternary amines. The resulting compounds are positively charged to a different degree depending on the ratio between the quaternary, primary and/or secondary amines within the formed conjugates. As such, the sphingoid-polyalkylamine conjugate exists as quaternized nitrogen salt including, but not limited to, quaternary ammonium chloride, a quaternary ammonium iodide, a quaternary ammonium fluoride, a quaternary ammonium bromide, a quaternary ammonium oxyanion and a combination thereof.

The sphingoid-polyalkylamine conjugate is preferably used in association with the nucleic acid molecule for the purpose of tranfecting the nucleic acid into a target cell. The term "association" preferably denotes electrostatic, dipole, acid-base as well as hydrophobic-hydrophobic interactions between the two components forming said lipoplex. However, the invention should not be limited by the particular type of association formed between the sphingoid-polyalkylamine conjugate and the nucleic acid molecule to be transfected. Thus, association means any interaction between the conjugate or the assembly formed therefrom and the nucleic acid molecule which is capable of achieving lipofection.

The lipoplex may be obtained by any method known in the art. This includes, without being limited thereto, post- or co-lyophilzation of the conjugate with the nucleic acid molecule, or by mere mixing of preformed sphingoid-polyamine conjugate assemblies with the nucleic acid molecule. Method for co-encapsulation are described, inter alia, in U.S. Pat. Nos. 6,156,337 and 6,066,331, while methods for post-encapsulation are described, inter alia, in WO03/000227, all incorporated herein by reference.

According to one embodiment, the lipoplex may be formed by incubation of the conjugate (which may be in the form of lipid assembly) with an appropriate amount of the nucleic acid molecule. The amount of the nucleic acid may vary considerably but is normally 0.05-2 μg per 35 mm Petri dish or 0.1 μg per well in 96 well plate. Conditions may also vary widely, and it is a routine matter and standard practice to optimize conditions for each type of cell. Optimization typically involves varying the conjugate to nucleic acid molecule ratio According to one preferred embodiment, the sphingoid-polyalkylamine conjugates form lipid assemblies. One example of a suitable assembly includes the formation of micelles or vesicles, and in particular, liposomes. The lipid assembly as used herein denotes an organized collection of lipid molecules forming inter alia, micelles and liposomes. The lipid assemblies are preferably stable lipid assemblies. "Stable lipid assembly" as used herein denotes an assembly being chemically and physically stable under storage conditions (4° C., in physiological medium) for at least one month.

The assemblies may include the sphingoid-polyalkylamine conjugate (non-methylated or methylated) as the sole lipid-like ingredient, or be combined with other helper lipid substances. Such other helper lipid substances may include non-cationic lipids like DOPE, DOPC, DMPC oleic acid or less polar lipids, such as cholesterol, at different mole ratios to the lipid-like compound. Cholesterol is one preferred added substance for in vivo application while DOPE may be a preferred helper lipid for in vitro applications. In this particular embodiment the mole ratio of cholesterol to cationic lipid is within the range of 0.01-1.0 and preferably 0.1-0.4.

The assemblies may also include enhancers (substances which enhance the activity of the lipid-like compounds when in the form of a lipoplex, which are not of lipidic nature) as known in the art, such as $CaCl_2$ and soluble polyamines.

According to one embodiment, the formed vesicles may be shaped as unsized heterogeneous and heterolamellar vesicles (UHV) having a diameter of about 50-5,000 nm. The formed UHV, may be downsized and converted to large unilamellar vesicles (LUV) having a diameter of about 50-100 nm or to small unilamellar vesicles <100 mm by further processing. The structure and dimensions of the vesicles, e.g. their shape and size may have important implications on their efficiency as vehicles for transfection of the nucleic acid molecule into the target cells, i.e. these determine their delivery properties.

It should be noticed that other components may be included in the lipid assembly, known to be used in structures of the like, such as steric stabilizers typically used with lipids. One example of a commonly used steric stabilizer are the lipopolymers, e.g. polyethylene glycol derivatized lipids (PEG-lipid conjugate), known to increase (extend) the circulation time of lipids.

Another important factor for efficient delivery is the ratio between the amount of the amine positive charge of the lipid-like ($L^+$) and the negatively charged oligo or polyanion complexed therein (or on the lipid-like surface) ($A^-$). The ratio determines the overall charge of the charged complex, where for effective delivery the ratio may be $1000<(L^+/A^-)<0.1$, preferably $20<(L^+/A^-)<1$ and more preferably $8<(L^+/A^-)<1.5$ depending on the entrapped moiety. According to one preferred embodiment, the conjugate's amino group to nucleic acid phosphate group ratio (+/−) is in the range. For transfection of cells with GFP or luciferase, a range of ratios 2.0-8.0 was used. For siRNA transfection the range was preferably between 2.0-5.0.

The present invention further provides a method for transfecting target cells with a nucleic acid (i.e. introducing the nucleic acid into the cell), said method comprises contacting said target cells with a sphingoid-polyalkylamine conjugate together with, preferably, in association with, a nucleic acid molecule, wherein said sphingoid-polyalkylamine conjugate comprises a sphingoid backbone carrying, via a carbamoyl bond, one or two, preferably one or two, polyalkylamine, thereby transfecting said cell with the nucleic acid molecule.

For the purpose of transfection, the sphingoid-polyalkylamine conjugate (either in the form of an individual compound or in the form of an assembly) may be associated with targeting substances. Targeting substances are known in the art and include, without being limited thereto, antibodies, a functional fragment of an antibody, a cell-surface recognition molecule, etc. the targeting substances may be attached to the polyalkylamine chain or directly to the lipid headgroup. For example, a sphingoid base/backbone may be derivatized with a hydrophilic polymer chain, as described above, and the hydrophilic polymer may be end-functionalized for coupling antibodies to its functionalized end. The functionalized end group may be a hydrazide or hydrazine group which is reactive toward aldehyde groups, although any of a number of PEG-terminal reactive groups for coupling to antibodies may be used. Hydrazides can also be acylated by active esters or carbodiimide-activated carboxyl groups. Acyl azide groups reactive as acylating species can be easily obtained from hydrazides and permit attachment of amino-containing molecules. The functionalized end group may also be 2-pyridyldithio-propionamide, for coupling an antibody or other molecule to the liposome through a disulfide linkage.

The invention also concerns pharmaceutical compositions for transfecting a nucleic acid into a target cell, the composition comprises an amount of a lipoplex, the lipoplex comprising: (i) a sphingoid-polyalkylamine conjugate comprising a sphingoid backbone carrying, via a carbamoyl bond, at least one, preferably one or two, polyalkylamine chains; and (ii) a nucleic acid molecule associated with said conjugate.

The amount of the lipoplex according to the invention should be effective to achieve delivery of the lipoplex into the target cells and once within the target cell, to produce a therapeutic effect. More particularly, the amount must be effective to achieve a measurable regulatory or biochemical effect on a biological target site to which the lipoplex is delivered. One example of a biological effect according to the invention includes the induction of apoptosis.

The composition preferably also comprises a physiologically acceptable carrier. The physiologically acceptable carrier according to the invention generally refers to inert, non-toxic solid or liquid substances preferably not reacting with the biologically active molecule or with the conjugate and which is required for the effective delivery of the conjugate with the biologically active molecule. The assemblies forming part of the composition of the invention are typically in the form of suspensions or dispersions.

Non-limiting examples of physiologically acceptable carrier include water, saline, 5% dextrose (glucose), 10% sucrose etc., either alone or with minor amounts (up to 10%) of an alcohol, such as ethanol.

The invention also concerns a method for the treatment of a disease or disorder, the method comprises providing a subject in need of said treatment an amount of a sphingoid-polyalkylamine conjugate associated with a nucleic acid molecule, the amount being effective to achieve transfection of a target cell (typically that associated with the disease or disorder) with the nucleic acid molecule and to achieve thereby a desired biochemical effect on said target cell. This method involves the administration of a lipoplex as defined above to a subject suffering from a disease, disorder pathological condition, or DNA deficiency.

A desired biochemical effect should be any effect resulting in the amelioration of undesired symptoms associated with a disease, the lessening of the severity or the curing of the disease, the improvement survival rate or more rapid recovery from the disease, or the prevention of the disease form occurring or a combination of two or more of the above.

The treatment may be facilitated by the providence to a subject in need of said treatment the pharmaceutical composition according to the invention. The pharmaceutical composition may be administered in various ways. Non-limiting examples of administration routes include oral, subcutaneous (s.c.), parenteral including intravenous (i.v.), intra-arterial (i.a.), intramuscular (i.m.), intraperitoneally (i.p.) and intranasal (i.n.) administration, as well as by infusion techniques. Those versed in the art will know how to modify the composition of the invention, typically being in the form of suspensions or dispersions, so as to be applicable for any of the above modes of administration.

Several methods of in vivo transfection/lipofection have been reported [Lasic DD. Liposomes in gene delivery. Boca Raton, Fla.: CRC Press, 1997; Dass C R. Int J Pharm 241:1-25 (2002)]. For example, the lipoplex may be injected into the blood stream of a subject, directly into a target tissue, into the peritoneum, instilled into the trachea, or converted to an aerosol, which the subject breathes. It is also possible to use a catheter to implant lipoplex assemblies in a blood vessel wall, which can result in successful transformation of several cell types, including endothelial and vascular smooth muscle cells.

Ex vivo lipofection is also included within the scope of the present invention. typically in ex vivo treatment bone marrow is removed from the patient and treated in culture under suitable conditions with the lipoplex according to the invention. After transfection, the transfected bone marrow is transplanted back into the patient's body.

An 18-mer antisense phosphorothioate oligonucleotide (S-ODN) targeted to 20 the first 6 codons of the open reading frame of bcl-2 was designed (Genta Inc.). In order to achieve efficient treatment, the antisense oligonucleaotide should be transferred into cancerous cells. Such targeting requires an appropriate vehicle. In an attempt to Ldentify the optimal system which delivers oligonucleotides into cells a particular conjugate was used, D-erythro-N-palmitoyl shingosyl-1-carbamoyl spermine termed in the following description by the abbreviation "CCS"), combination with DOTAP, DOPE, DOPC, cholesterol to form lipoplexes and lipid assemblies (e.g. liposomes).

The invention also concerns the use of the conjugate of the invention as a capturing agent. According to a specific embodiment of the invention, the conjugate may form part of a kit for research purposes.

The following description presents non-limiting examples of some transfection applications of the lipid-like vehicles of the present invention.

Figure 2:
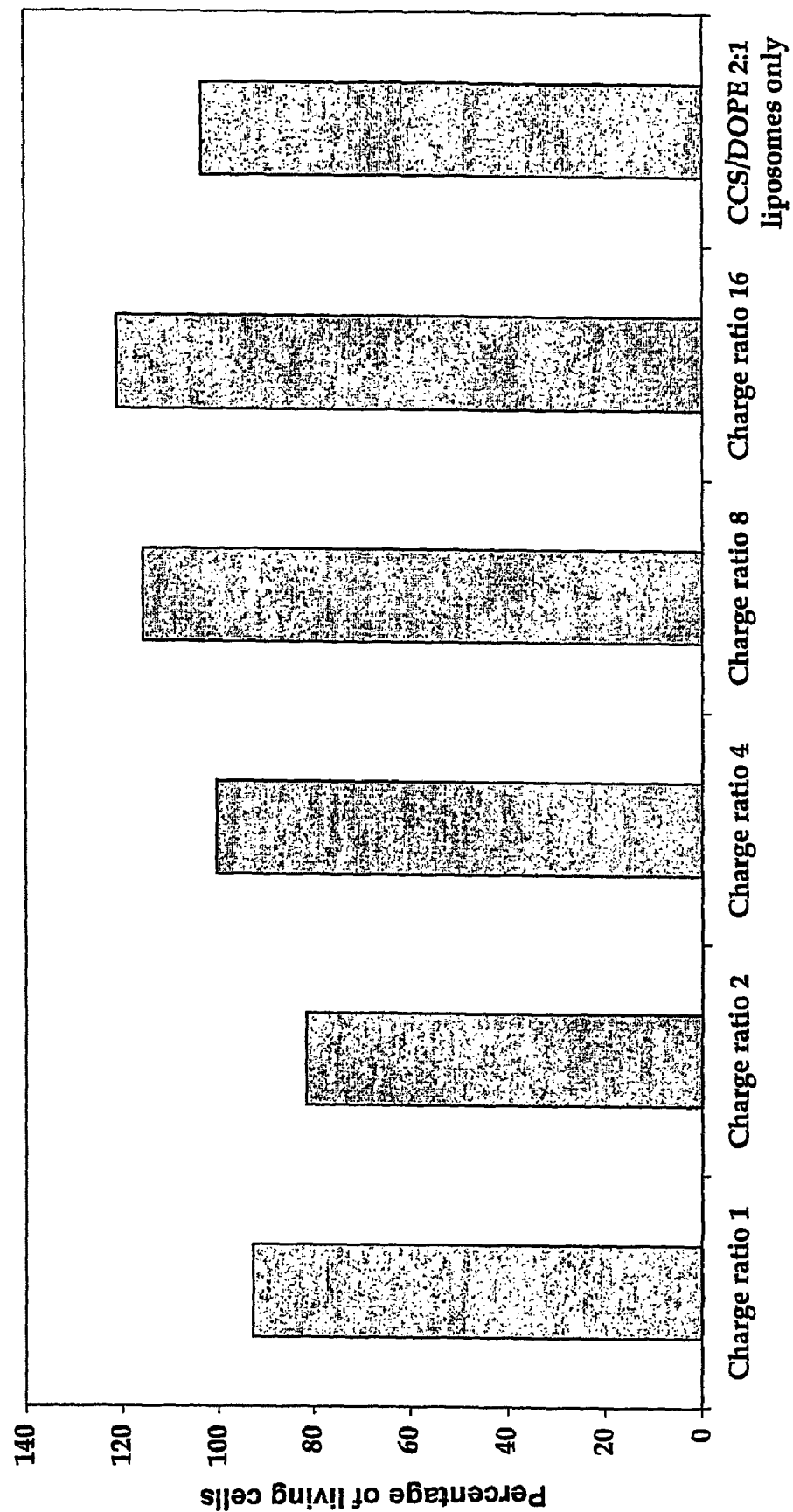
FIG. 2 shows toxicity studies on NIH 3T3 cells revealing that the CCS vehicles are non toxic to cells.

FIG. 2 exhibits the results of a toxicity assay including treatment of NIH 3T3 cells with different CCS/DOPE (2:1) lipoplexes with the indicated lipid/DNA charge ratios (1, 2, 4, 8, 16) or with the CCS/DOPE (2:1) assemblies only (i.e. without DNA). This Figure clearly demonstrates that the CCS/DOPE (2:1) assemblies in the chloride form of positively charged amine groups, were not toxic (no toxicity being presented by 100% living cells) when added to NIH 3T3 cells in the amounts used in transfection, either as free assemblies or in the form of lipoplexes with luciferase plasmid as described below.

Figure 3:
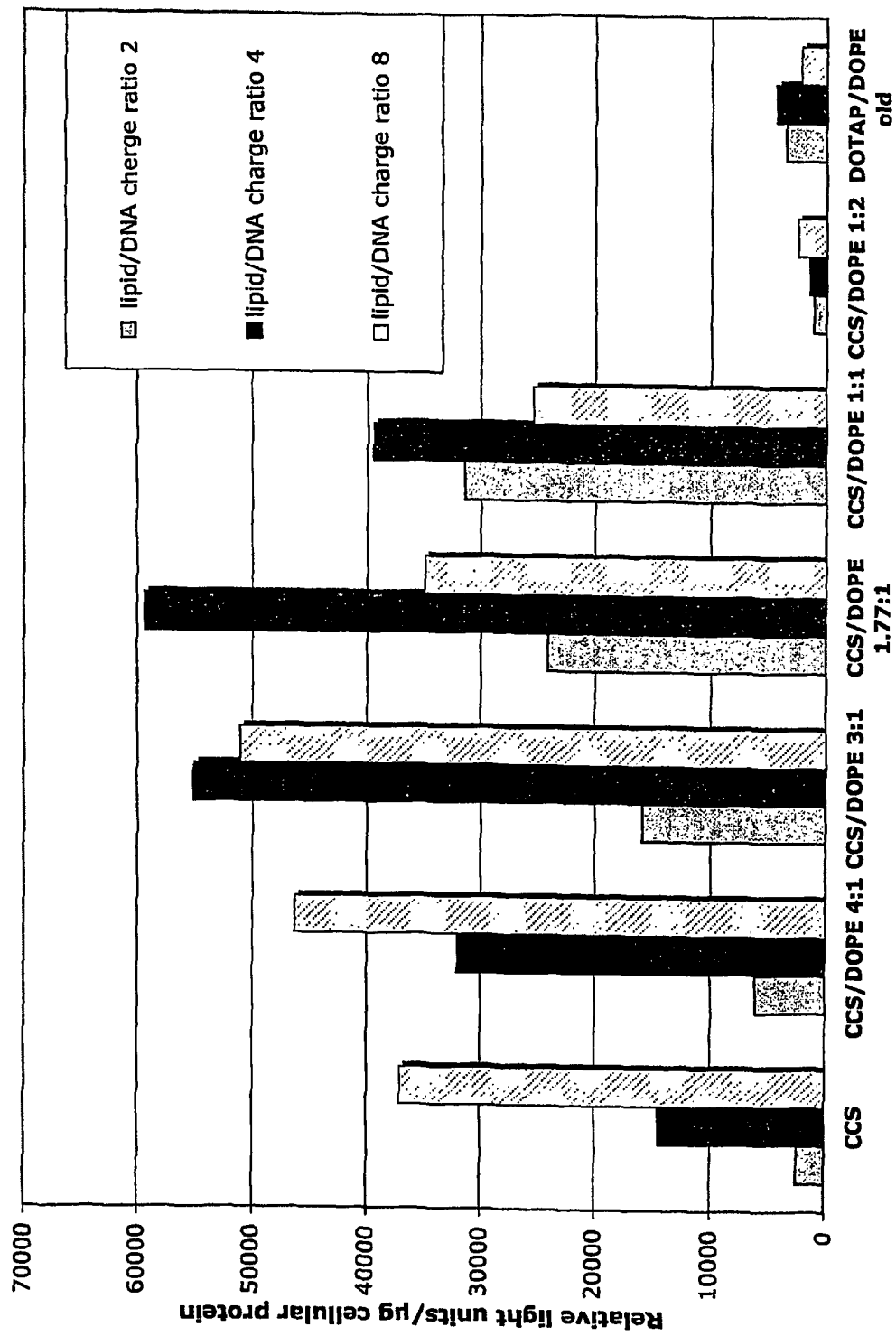
FIG. 3 shows gene transfection of luciferase plasmid into NIH 3T3 cells. Transfection was carried by CCS/DOPE vehicles.

Turning to FIG. 3, effective transfection of luciferase into NIH 3T3 cells is demonstrated. The vehicle used UHV composed of a a mixture of the CCS together with the commercial helper lipid DOPE at the indicated ratios (CCS/DOPE). In addition, different lipid/DNA charge ratios were examined. As indicated in FIG. 3, a CCS/DOPE ratio greater than 1 was effective as a DNA transfection vehicle, at all tested lipid/DNA charge ratios.

Transfection into C-26 cells using CCS vehicles was also examined and the transfection efficacy was compared with that obtained by an optimal formulation with the commercially available vehicle FuGENE6® (Rocsh Diagnostic GmbH Manheim Germany, used according to manufacturer's instructions).

Figure 4:
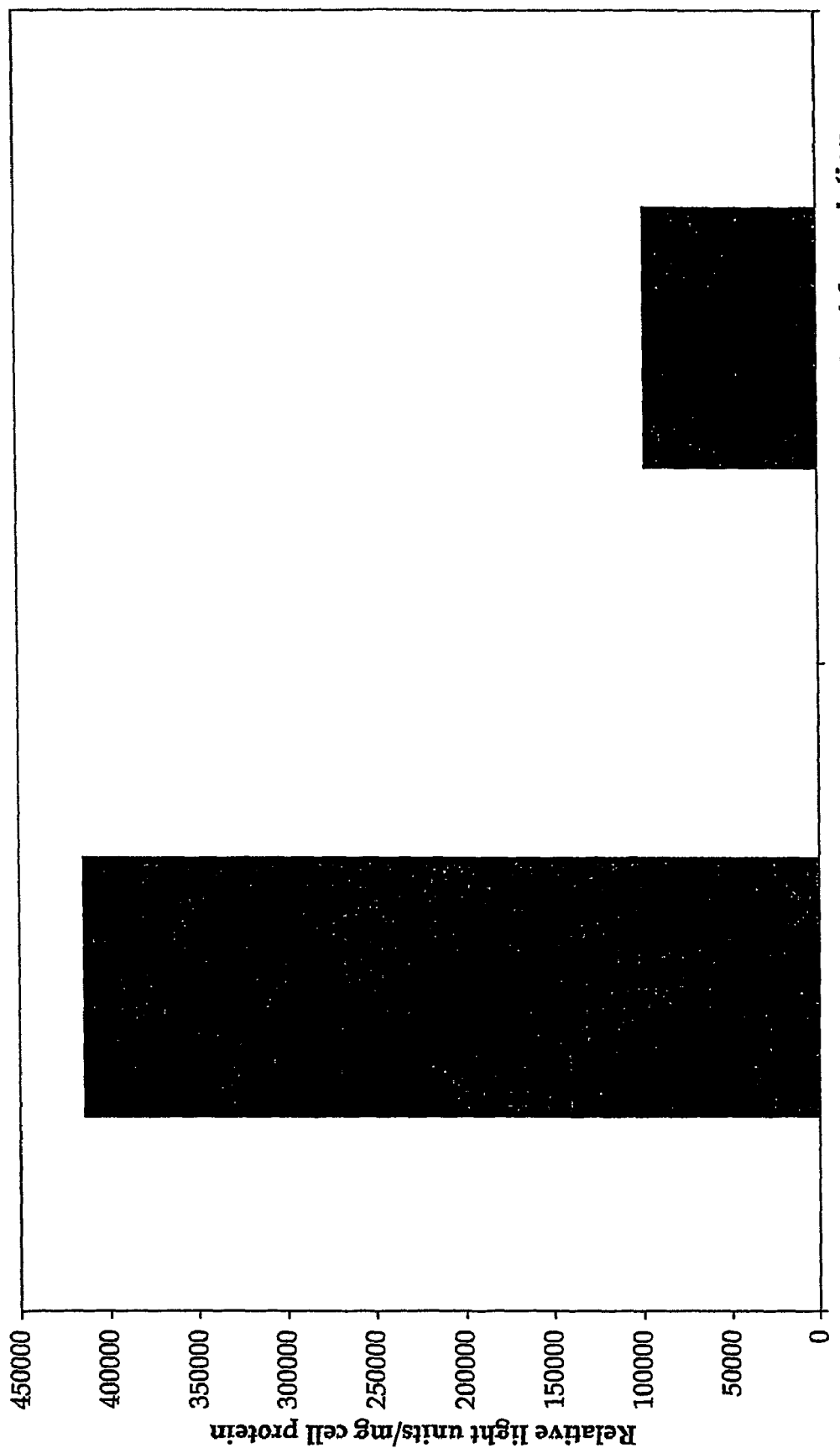
FIG. 4 shows a comparison of transfection of C-26 cells with luciferase according to the method described herein and transfection with an optimal formulation of FuGENE6®.

FIG. 4 presents a comparison between luciferase transfection with the CCS/DOPE (2:1) assembly and that performed with FuGENE6®. As clearly shown, transfection with the CCS/DOPE (2:1) assembly was more effective as compared to the commercial vehicle.

Figure 5:
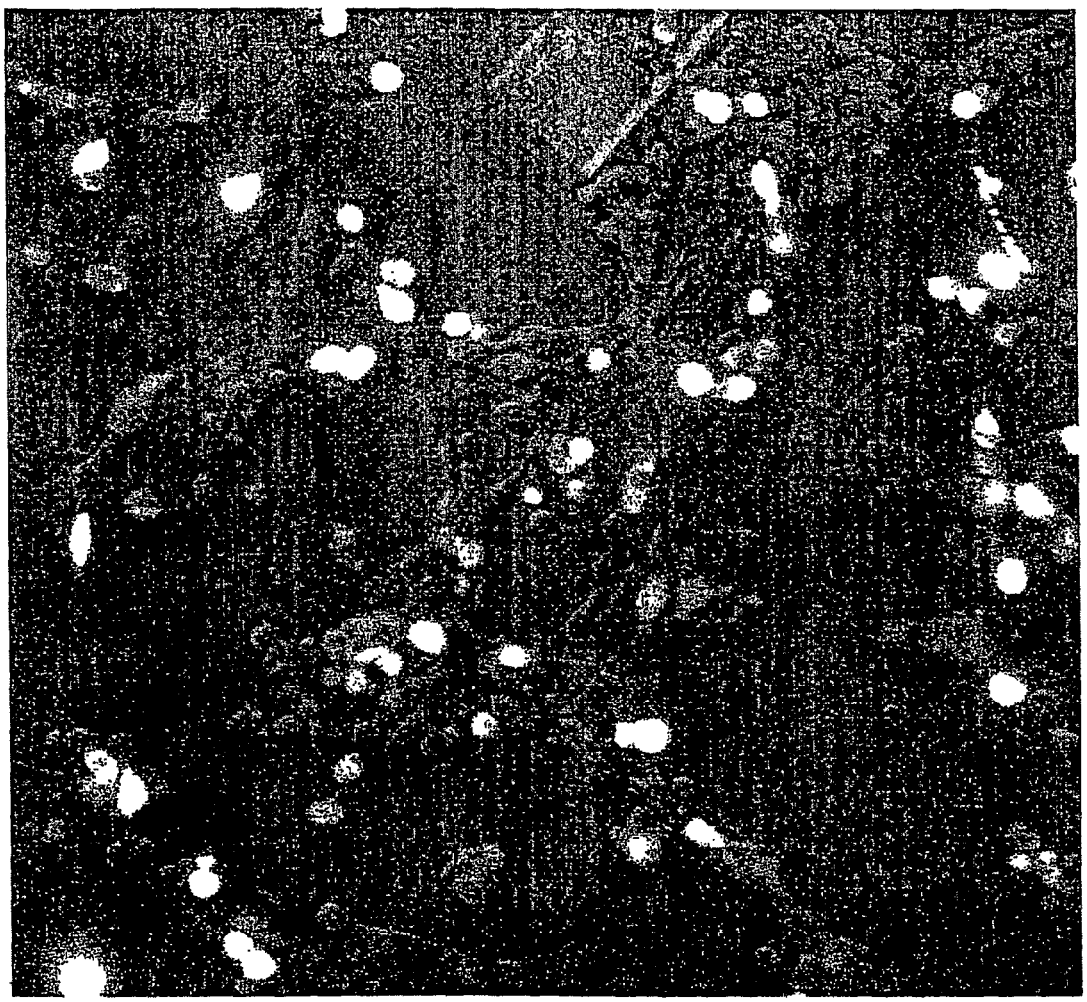
FIG. 5 visualizes the efficiency of transfection of pGFP (white spots) into NIH 3T3 cells using a mixture of LLC vehiclesCCS/DOPE in a 2:1 ratio and complexed to the plasmid pQBI-25 coding for green fluorescent protein (GFP) (Qbiogene, Montreal, Canada. The figure shows that there is a high percentage of GFP expressing cells in the cell population.

FIG. 5 shows a pictorial demonstration of the efficiency of transfection of pGFP into NIH 3T3 cells using a mixture of CCS/DOPE in a 2:1 ratio and complexed to the plasmid pQBI-25 coding for green fluorescent protein (GFP) (Qbiogene, Montreal, Canada).

In a further assay, the following anti-Bcl-2 siRNA complexes with CCS/DOTAP based lipoplexed were prepared. Table presents the different types of lipoplexes:

TABLE 1

Anti-Bcl-2 siRNA CCS/DOTAP lipoplexes

| Cationic assemblies composition | Type of siRNA | siRNA P$^-$/ cationic lipid ratio | Free siRNA (%) |
|---|---|---|---|
| CCS | I | ½ | 0 |
| CCS | II | ½ | 0 |
| DOTAP | I | ½ | 0 |
| DOTAP | II | ½ | 14 |
| CCS/DOPE (2:1) | I | ½ | 0 |
| CCS/DOPE (2:1) | II | ½ | 0 |
| DOTAP/DOPE (2:1) | I | ½ | 0 |
| DOTAP/DOPE (2:1) | II | ½ | 15 |
| CCS/Cholesterol (2:1) | I | ½ | 0 |
| CCS/Cholesterol (2:1) | II | ½ | 0 |
| DOTAP/Cholesterol (2:1) | I | ½ | 20 |
| DOTAP/Cholesterol (2:1) | II | ½ | 15.5 |

The results presented above teach that while the level of association of siRNA with DOTAP liposomes is not always complete, the CCS micelles or CCS/DOPE or CCS/CHOL assemblies, at the indicated ratios, bind siRNA with 100% efficiency.

Figure 6:
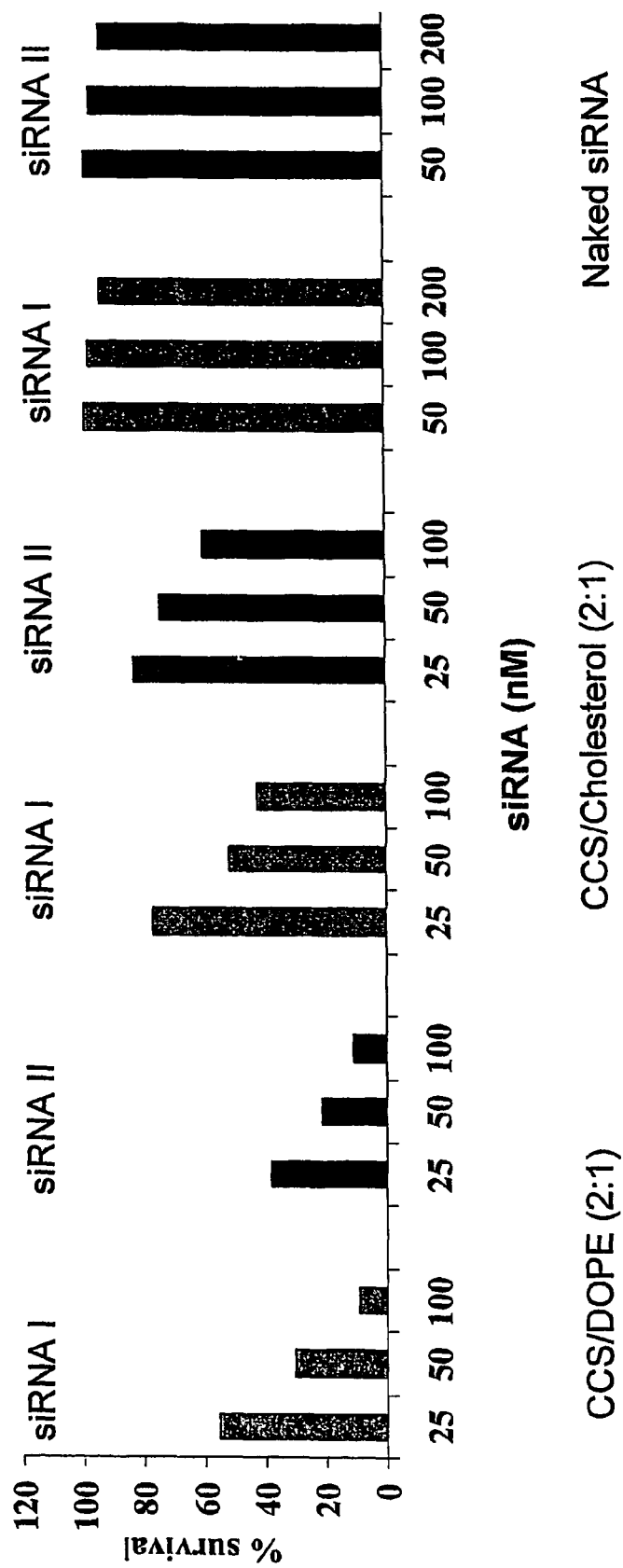
FIG. 6 shows the % survival of MCF-7 cells incubated for 72 hr with CCS liposomes, CCS/DOPE (2:1) or CCS/Cholesterol (2:1) containing Bcl-2 siRNA I/II or with naked Bcl-2 siRNA I/II.
Figure 7:
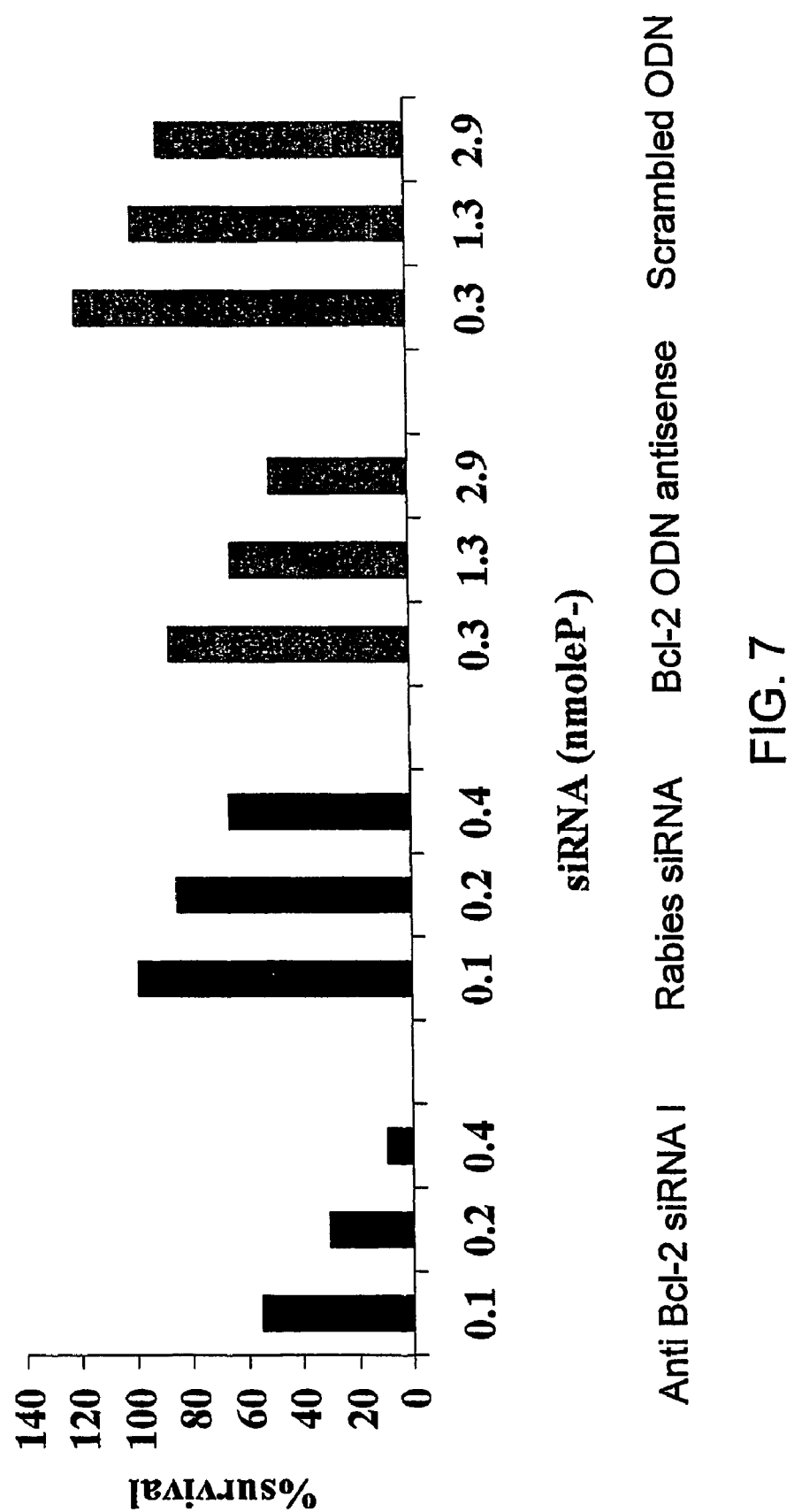
FIG. 7 shows the % survival of MCF-7 cells incubated for 72 hr with cationic liposomes: CCS/DOPE (2:1) complexed with one of the following: antisence Bcl-2 siRNA I, Rabies siRNA, Bcl-2 ODN antisense, or scrambled ODN at a charge ratio +/− of 2:1.
Figure 8:
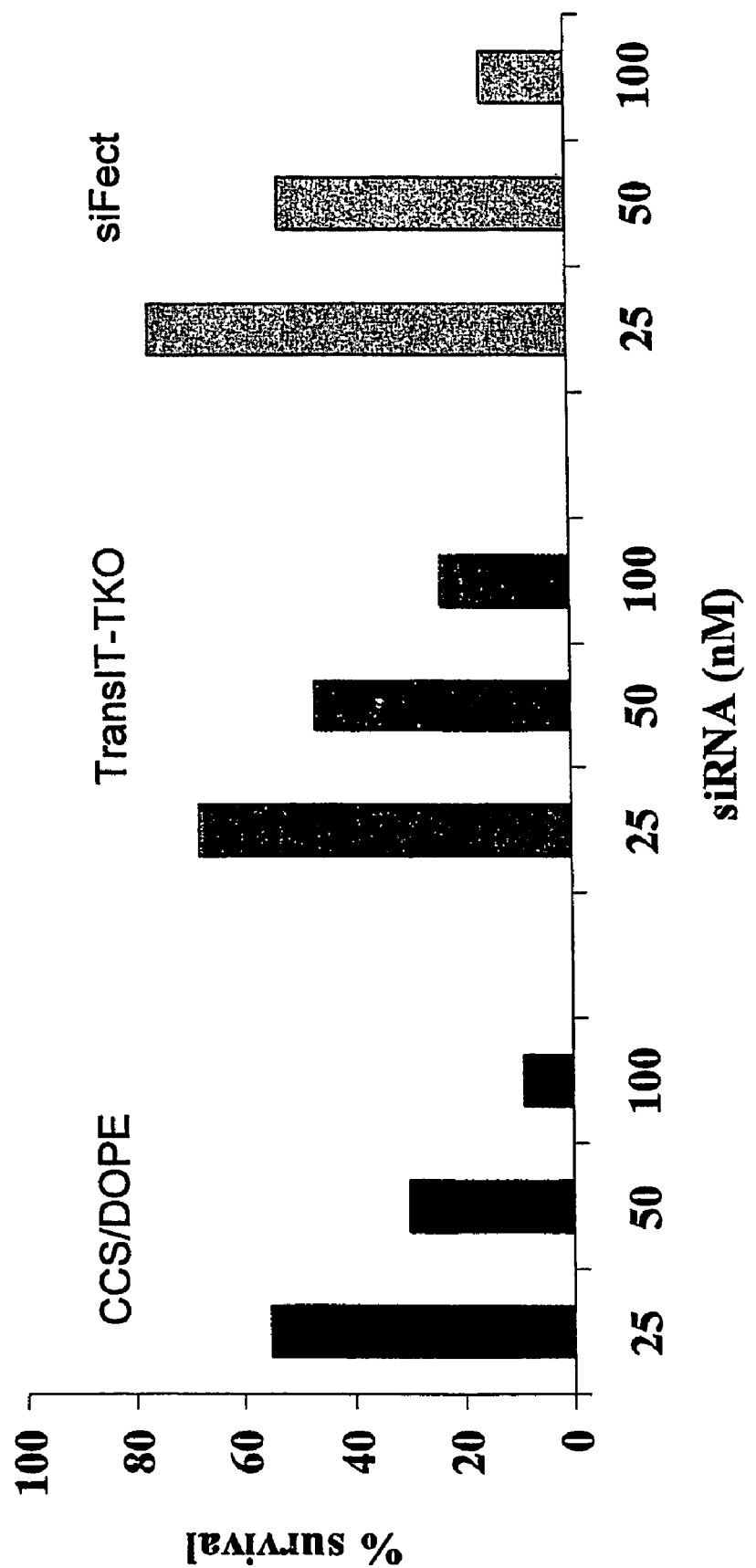
FIG. 8 shows the % survival of MCF-7 cells incubated for 72 hr with either CCS/DOPE (2:1), or with commercially available kits TransIT-TKO (Mirus, Madison, Wis.) or siFECT (Promega, Madison Wis.) complexed with siRNA (Bcl-2).

FIGS. 6-8 present the % survival of MCF-7 cells treated with the indicated cationic lipid assemblies or with naked siRNA.

In particular, FIG. 6 shows % survival of the cells treated with cationic lipid assemblies associated with Bcl-2 siRNA (siRNA I or siRNA II as described in the Materials and Methods). The different lipid assemblies examined are CCS in combination with DOPE (ratio 2:1), CCS in combination with cholesterol (ratio 2:1). The results show that as compared to the naked siRNA, the CCS based assemblies were more effective in transfecting the cells with the nucleic acid molecule.

Turning to FIG. 7, this figure shows % survival of the cells treated with CCS/DOPE combination (ratio 2:1) containing Bcl-2 siRNA, Bcl-2 antisense (as described in the Materials and Methods) for 72 hours. The results presented show that CCS based assemblies were efficient in delivering anti-Bcl-2 siRNA I, which is specific to MCF-7 cells and thereby reducing cell survival, as compared to the effect obtained with the non-specific nucleic acid molecules: Rabies siRNA, Bcl-2 ODN or Scrambled ODN.

FIG. 8 shows a comparison between % survival of the MCF-7 cells treated with either CCS based lipid assemblies combined with DOPE, or with the commercially available carriers: TransIT-TKO or siFect, associated with siRNA (as described in the Materials and Methods). The results show that CCS/DOPE assemblies were efficient as carriers of the Bcl-2 siRNA I molecule into the cells.

SPECIFIC EXAMPLES

Chemistry
Synthesis of N-palmitoyl D-erythro Sphingosyl-1-carbamoyl spermine (CCS)

(i) N-palmitoylsphingosine (1.61 g, 3 mmol) was dissolved in dry THF (100 ml) with heating. The clear solution was brought to room temperature and N,N'-disuccinimidyl carbonate (1.92 g, 7.5 mmol) was added. DMAP (0.81 g, 7.5 mmol) was added with stirring and the reaction further stirred for 16 hours. The solvent was removed under reduced pressure and the residue re-crystallized from n-heptane yielding 1.3 g (68%) of disuccinimidylceramidyl carbonate as white powder m.p. 73-76° C.

(ii) Spermine (0.5 g, 2.5 mmol) and the disuccinimidylceramidyl carbonate (0.39 g, 0.5 mmol) were dissolved in dry dichloromethane with stirring and then treated with catalytic amount of 4-dimethylamino pyridine (MAP). The solution was stirred at room temperature for 16 hours, the solvent evaporated and the residue treated with water, filtered and dried in vacuo, giving 0.4 g (82%) of crude material which was further purified by column chromatography on Silica gel, using 60:20:20 Butanol: AcOH:H$_2$O eluent.

(iii) For obtaining a quaternary amine within the compound, the product of step (ii) may be methylated with DMS or CH$_3$I.

The structure of CCS was confirmed by $^1$H— and $^{13}$C-NMR spectrometry (data not shown).

Other Synthetic Procedures

Similarly to the above procedure, the following procedures may be applied:

Synthesis of Linear Monosubstituted Ceramde-spermine Conjugate as Depicted in FIG. 1A An equivalent of a ceramide is reacted with 2.5 equivalents of disuccinimidyl carbonate in the presence of DMAP to obtain the corresponding 1,3-di-O-succinimidyl derivative is obtained.

The disuccinimidyl derivative though obtained is reacted with an equivalent of spermine at room temperature using catalytic amount of DMAP to obtain the 3-monosubstituted ceramide-spermine conjugate of FIG. 1B.

Synthesis of Linear Disusbstituted Ceramide-spermine Conjugate as Depicted In FIG. 1B An equivalent of 1,3-di-O— succinimidyl sphingoid derivative prepared as described above is reacted with 2.5 equivalents of spermine at 80° in the presence of catalytic amounts of DMAP. The 1,3-disubstituted CCS is though obtained.

Synthesis of Linear Disusbstituted Ceramide-branched Spermine Conjugate as Depicted in FIG. 1C An equivalent of 1,3-di-O— succinimidyl ceramide derivative prepared as described above is reacted with 2.5 equivalents of alpha-omega di protected spermine at 80° in the presence of catalytic amounts of DMAP.

The protection is removed and the 1,3-"branched" disubstituted ceramide-spermine conjugate is obtained.

Synthesis of Linear Disusbstituted Ceramide-cyclic Spermine Conjugate as Depicted in FIG. 1D An equivalent of 1,3-di-O-succinimidyl ceramide derivative prepared as described above is reacted with 0.75 equivalents of spermine at 80° C. in the presence of catalytic amounts of DMAP.

DOPE

Dioleoylphosphatidylethanol-amine (DOPE) was purchased from Lipoid, (Ludwigshafen, Germany) or from Avanti polar lipids (ALABASTER USA)

DOTAP was purchased from Avanti polar lipids (ALABASTER USA);

Cholesterol was purchased from Sigma.

S-ODN

Phosphorothioate antisense 18-mer G3139 [S-d-5'-(TCT CCC AGC GTG CGC CAT)] (SEQ ID NO:1) was obtained from Genta Inc. Lexington, MA. Its purity was assessed by HPLC (Merck Hitachi D-7000) incorporating an anion exchange column. A gradient of ammonium acetate in 50% isopropanol in a pH 8 buffer was employed.

Cell Culture

For siRNA efficiency and for transfection efficiency in cell culture, MCF-7 cells of NIH 3T3 cells respectively were grown in 75-ml cell culture flasks (NalgeNunc, Rochester, N.Y.) in DMEM supplemented with 2 mM L-glutamine, 100 IU/ml penicillin-streptomycin, 4.5 g/L D-glucose, 1 mM sodium pyruvate and 10% v/v fetal calf serum. For lipoplex studies, the MCF-7 cells were cultivated as above with the exception that no pyruvate was incorporated. The cells were grown to ~90% confluency in 75 cm$^2$ flasks. The cells were regularly split and were never allowed to grow to more than 80% confluence. Only cells that had undergone fewer than 25 passages were used for transfection. The cell medium consisted of DMEM (NIH 3T3) or RPMI (C-26, MCF-7) supplemented with 0.2 mM L-glutamine, 10% (w/w) fetal calf serum, 1 mg/ml penicillin, and 100 U/ml streptomycin (Biological Industries, Beth Haemek, Israel. All components of the cell culture medium were acquired from Biological Industries (Kibbutz Beit Haemek, Israel).

Luciferase Assay

Luciferase activity was assayed on cell extracts using Bright-Glo™ Luciferase Assay system (Promega, Madison Wis.). Briefly, cells were washed twice with cold PBS×1 and lysed for 10 min with Cell Culture Lysis Buffer (Promega). Then, cells were harvested and centrifuged for 5 min to remove cell debris. Luciferase activity in relative light units was assayed on cell extracts using Bright-Glo Luciferase Assay System (Promega, Madison, Wis.) (10 µl cell extract per 30 µl luciferase substrate) by a plate-reading luminometer Mithras LB 940(Berthold Technologies, Bad Wildbad, Germany). The amount of luciferase was normalized to the amount of total protein in the lysate, which was determined by Lowry method.

In a similar assay, transfection was performed with lipoplexes prepared from CCS (chloride salt)/DOPE (2:1) unsized (non-extruded) assemblies and plasmid coding for luciferase gene under CMV promoter and compared with lipoplexes from FuGENE6 transfection reagent (ROCHE, Mannheim, Germany).

Methylene Blue Assay of Cell Survival

Cytotoxicity was tested by the methylene blue (MB) staining assay [Elliott W M and Auersperg N. Biotech Histochem 68:29-35 (1993)]. In general, a known number of exponentially growing cells in 200 µL of medium were plated in 96-microwell, flat-bottomed plates. For each of the lipoplexes tested, 3 wells were used. Following 24 h of incubation in culture, 20 μL of different concentrations of various lipoplexes were added to each well containing untreated cells. Normal saline was added to the controls. Cells were exposed to lipoplex for 24 h. At the end of exposure the treated cells, as well as parallel control cells were washed and fixed by adding 50 μL of 2.5% glutaraldehyde to each well for 15 min. Fixed cells were rinsed 10 times with deionized water and once with borate buffer (0.1 M, pH 8.5), dried, and stained with MB (100 μL of 1% solution in 0.1 M borate buffer, pH 8.5) for 1 h at r. t. Stained cells were rinsed thoroughly with de-ionized water to remove any non-cell-bound dye and then dried. The MB bound to the fixed cells was extracted by incubation at 37° C. with 200 μL of 0.1 N HCl for 1 h, and the net optical density of the dye in each well was determined by a plate spectrophotometer (Labsystems Multyskan Bichromatic, Finland) at 620 nm.

Preparation of Assemblies from Cationic Lipids

For all preparations water purified with WaterPro PS HPLC/UV Ultrafilter Hybrid model (LABCONCO, Kansas City, Mo.) was used, which delivers Type I, 18.2 megaohm/cm, sterile (pyrogen-free to 0.06 e.u./ml) water. Briefly, lipids stocks were mixed at a room temperature in a common solvent, usually tert-butanol (freezing point=22° C.) or a mixture of tert-butanol/water (1:1 v/v). The lipid mixture was freeze-dried overnight in tertiary butanol to obtain dry lipid "cake". The cake was hydrated by addition of aqueous vehicle, usually 20 mM Hepes buffer, pH 7.4, or DDW, or 5% dextrose, and the dispersion was vortexed for 5 min. This procedure produced unsized heterogeneous vesicles (UHV). The volume of hydration step was adjusted to control the final concentration of lipid cationic charges, usually from 1 mM to 20 mM.

For downsizing, whenever desired, the aqueous lipid dispersions were extruded stepwise with LiposoFast extruder (Avestin, Ottawa, Canada) through polycarbonate filters starting with a pore size of 400 nm, followed by 100-, 50- or 30-nm extrusion step. For certain formulations, the downsizing was by sonicating lipid dispersions in a bath sonicator until solution became clear.

Lipid assemblies as well as Liposomes were prepared by dissolving in tert-butanol one of the following cationic lipids (DOTAP: 1,2-dioleoyl-3-trimethy:ammonium-propane, N-palmitoyl D-erythro sphingosyl carbamoyl-spermine (CCS), or a mixture of the cationic lipid with a neutral co-lipid (DOPC-1,2-dioleoyl-sn-glycero-3 phosphatidyl-choline, DOPE-dioleoylphosphatidylethanol-amine) or cholesterol in a 1:1 mole ratio. In all cases, the prepared assemblies were stored at 4° C.

Just before their addition to cells, small volumes of assemblies' dispersion were diluted with pre-calculated amounts of 20 mM Hepes buffer (pH 7.4) in order to produce aliquots containing the appropriate amount of cationic lipid.

Preparation of Lipoplexes Containing Oligonulcleotides (ODN)

For the preparation of the lipoplexes, the diluted assemblies dispersions (either UHV or LUV) obtained as described above were added to solutions comprising an 18-mer anti-sense phosphorothioate oligonucleaotide (S-ODN), appropriately diluted in 20 mM Hepes buffer at pH 7.4, in glass vials at the appropriate $L^+/ODNP^-$ mole ratio. The procedure was the same as for preparation of plasmid lipoplexes (below).

It should be noted that the CCS conjugate exhibits an equivalent of between one and three positive charges and this was taken into consideration for calculating $L^+$.

Preparation of Lipoplexes Containing Plasmid DNA

For cell culture transfections and most of the biophysical studies lipoplexes were prepared as follows: DNA was diluted in Hepes buffer to a concentration of 0.2 mM phosphate, and cationic lipid was diluted in a separate tube to a concentration of 0.2-2 mM positive charge. The final concentration of lipid was adjusted so as to make its volume equal to that of DNA. To prepare the lipoplexes, DNA was added dropwise to the lipid to achieve a desired cationic lipid/DNA charge ratio. For example, to prepare lipoplexes at +/−ratio 2.0, 1, 65 μg DNA (5 nmol) in a 90-μl volume were added to 10 nmol of cationic lipid in the same volume. The resulting lipoplexes were incubated for 15-20 min without agitation. The final concentration of nucleic acid in the formulation (before addition to cell medium) was 0.01 mg/ml.

Preparation of Lipoplexes Containing siRNA

For the preparation of lipoplexes containing siRNA, 20 μM (equivalent to 822 μM of negatively charges phosphate ($P^-$)) stock solution of siRNA was diluted in 100 μl of DDW which contained 5% dextrose (final concentration of siRNA $P^-$ 82 μM).

Lyophilized cationic lipids were hydrated with 100 μl of DDW which contained 5% dextrose (final concentration 164 μM total lipids).

siRNA (100 μl) was added dropwise to 100 μl of lipid solution and incubated for 10 minutes (final concentration of siRNA $P^-$ 41 μM and of lipids 82 μM). siRNA (25, 50 and 100 nM) was complexed with 2, 4 and 8 μM lipids in parallel and incubated for 48-72 hours.

Lipofection

Lipofection of Plasmid DNA

Twenty four hours prior to transfection each flask with cells was washed once with PBS, cells were detached with 5 ml trypsin for 3 min, diluted with 20 ml fresh medium and plated at a density of $7 \times 10^3$ cells/well in 96-well plates or $1.3 \times 10^5$ cells/well in 35 mm Petri dishes. On the day of transfection, the old medium was replaced with fresh medium and lipoplexes were homogeneously added to the wells, 0.2 μg DNA (10 μl lipoplexes) per well of 96-well plate, or 1 μg (50 μl) per 35-mm plate. The transfection efficiency was measured according to the reporter gene, usually 24-48 h post-transfection.

S-ODN

Lipofection of S-ODN was performed in a manner similar to that described with respect to the plasmid DNA with the following differences:

Treatment solutions contained S-ODN (generally 0.005 nmol unless otherwise stated), either free or as freshly prepared lipoplexes; or alternatively the control liposome solutions containing equivalent amounts of cationic lipid.

In all cases, cells were incubated for 96 h at 37° C., 90% relative humidity and 5% $CO_2$.

Each specific treatment solution was added to three different wells and the entire experiment was performed in triplicate, siRNA MCF-7 cells were plated into 96 well plate at density of $4*10^3$ cells/well and allowed to grow for 24 hr. After indicated time period, various lipoplexes at the cationic lipid/siRNA $P^-$ ratio of 2:1 were added into the cells and incubated for 72 hr.

Two different types of siRNA (Dharmacon, USA) were used:
siRNA I (19 nucleotides, MW=13.600)
siRNA II (22 nucleotides, MW=14.025)
Additional controls include:
Comparison with the carriers TransIT-TKO (Mirus, USA) and siFect™ (Promega, USA) commercial kits.
18 mer G3139 Bcl-2 ODN antisense (Genta, Lexington, Ma)
Scrambled antisense (Genta Lexington, Ma).
Rabies virus siRNA (Mirus, USA or Promega, USA)
Following 72 hr of growth, cells were fixed by 2.5% glutaraldehyde and stained with MB. The MB bound to the fixed cells was extracted by 0.1 N HCl, and the net optical density of the dye in each well was determined by a plate spectrophotometer (Labsystems Multyskan Bichromatic, Finland) at 620 nm.

Quantification of siRNA Complexation with Cationic Lipid Assemblies

Different amounts of cationic LUV (16.4-41 nmole lipid) were mixed with 8.2 nmole siRNA P-to achieved various siRNA P-/lipid/mole ratio. Free siRNA (8.2 nmole) was used as a control. After 10 min of incubation at room temperature, 2.5 nmole ethidium bromide (EtBr) was added to each sample, followed by additional 10 min if incubation. EtBr fluorescence intensity was measured using an excitation wavelength of 260 nm and emission wavelength of 591 nm, using a cutoff filter of 515 nm.

Each sample was corrected for the background fluorescence of EtBr in the absence of siRNA. The fluorescence intensity was express as the % of maximum fluorescence signal obtained for the same concentration (8.2 nmole) of free siRNA P-.

The invention will now be defined by the appended claims, the contents of which are to be read as included within the disclosure of the specification.

The invention claimed is:

1. A method for transfecting a cell with a nucleic acid molecule comprising contacting said cell with a sphingoid-polyalkylamine conjugate together with said nucleic acid molecule, wherein said sphingoid-polyalkylamine conjugate has the following formula (I):

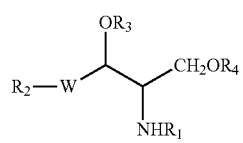

wherein
$R_1$ represents a hydrogen, a branched or linear alkyl, aryl, alkylamine, or a group —$C(O)R_5$;

$R_2$ and $R_5$ represent, independently, a branched or linear $C_{10}$-$C_{24}$ alkyl, alkenyl or polyenyl group;

$R_3$ and $R_4$ represent a group —$C(O)$—$NR_6R_7$, in which $R_6$ and $R_7$, being the same or different for $R_3$ and $R_4$, represent, independently, a hydrogen, or a saturated or unsaturated branched or linear polyalkylamine, wherein one or more amine units in said polyalkylamine may be a quaternary ammonium; or $R_3$ and $R_4$ form, together with the oxygen atoms to which they are bound, a heterocyclic ring comprising —$C(O)$—$NR_9$-$[R_8$—$NR_9]_m$—$C(O)$—, in which $R_8$ represents a saturated or unsaturated $C_1$-$C_4$ alkyl and $R_9$ represents a hydrogen or a polyalkylamine of the formula —$[R_8$—$NR_9]_n$—, wherein said $R_9$ or each alkylamine unit —$R_8NR_9$ may be the same or different in said polyalkylamine; and n and m represent, independently, an integer from 1 to 10; and W represents a —CH=CH—, —$CH_2$—CH(OH)— or —$CH_2$—$CH_2$—group.

2. The method of claim 1, wherein said nucleic acid is associated with said sphingoid-polyalkylamine conjugate.

3. The method of claim 1, wherein said nucleic acid molecule is a plasmid DNA.

4. The method of claim 1, wherein said nucleic acid molecule is a small interference RNA (siRNA).

5. The method of claim 1, wherein said nucleic acid molecule is an oligodeoxynucleotide (ODN).

6. The method of claim 2, wherein said sphingoid-polyalkylamine conjugate forms lipid assemblies.

7. The method of claim 6, wherein said sphingoid-polyalkylamine conjugate forms vesicles, micelles or a mixture of same.

8. The method claim 1, wherein the sphingoid backbone is selected from ceramide, dihydroceramide, phytoceramide, dihydrophytoceramide, ceramine, dihydroceramine, phytoceramine, dihydrophytoceramine.

9. The method of claim 1, wherein said sphingoid backbone is a ceramide.

10. The method of claim 1, wherein said polyalkylamine chains are independently selected from the group consisting of spermine, spermidine, a polyalkylamine analog and a combination thereof.

11. The method of claim 1, wherein $R_1$ represents a —C(O)$R_5$ group, $R_5$ being as defined.

12. The method of claim 1, wherein said $R_2$ and $R_5$ represent, independently, a linear or branched $C_{12}$-$C_{18}$ alkyl or alkenyl chain.

13. The method of claim 1, wherein W represents —CH=CH—.

14. The method of claim 1, wherein $R_1$ represents a —C(O)$R_5$ group; $R_5$ represents a $C_{12}$-$C_{18}$ linear or branched alkyl or alkenyl; W represents —CH=CH—; $R_2$ represents a $C_{12}$-$C_{18}$ linear or branched alkyl or alkenyl; $R_3$ and $R_4$ represent, independently, a group —C(O)—NR$_6$R$_7$, wherein $R_6$ and $R_7$ represent, independently, a hydrogen or a polyalkylamine having the general formula (II):

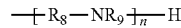

wherein $R_8$ represent a $C_1$-$C_4$ alkyl;

$R_9$ represents a hydrogen or a polyalkylamine branch of formula (II), said $R_8$ and $R_9$ may be the same or different for each alkylamine unit, —$R_8$N$R_9$—, in the polyalkylamine of formula (II); and n represents an integer from 3 to 6, wherein $R_6$ and $R_7$ are not both hydrogen in the same moiety.

15. The method of claim 1, wherein both $R_3$ and $R_4$ represent the same or different polyalkylamine.

16. The method of claim 1, wherein $R_1$ represents a —C(O)$R_5$ group; $R_5$ represents a $C_{12}$-$C_{18}$ linear or branched alkyl or alkenyl; W represents —CH=CH—; $R_2$ represents a $C_{12}$-$C_{18}$ linear or branched alkyl or alkenyl; $R_3$ and $R_4$ represent, independently, a group —C(O)—NR$_6$R$_7$, wherein $R_6$ and $R_7$ represent, independently, an alkylamine or a polyalkylamine having the general formula (II):

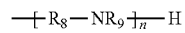

wherein $R_8$ represents a $C_1$-$C_4$ alkyl;

$R_9$ represents a hydrogen or a polyalkylamine branch of formula (II), said $R_8$ and $R_9$ may be the same or different for each alkylamine unit, —$R_8$N$R_9$—, in the polyalkylamine of formula (II); and n represents an integer from 3 to 6.

17. The method of claim 1, wherein $R_1$ represents a —C(O)$R_5$ group; $R_5$ represents a $C_{12}$-$C_{18}$ linear or branched alkyl or alkenyl; W represents —CH=CH—; $R_2$ represents a $C_{12}$-$C_{18}$ linear or branched alkyl or alkenyl; $R_3$ and $R_4$ form, together with the oxygen atoms to which they are bonded, a heterocyclic ring comprising —C(O)—[NH—$R_8$]$_n$—NH—C(O)—, wherein $R_8$ represents a $C_1$-$C_4$ alkyl, wherein for each alkylamine unit —NH—$R_8$—, said $R_8$ may be the same or different; and n represents an integer from 3 to 6.

18. The method of claim 1, wherein said $R_8$ is a $C_3$-$C_4$ alkyl.

19. The method of claim 1, wherein said sphingoid-polyalkylamine conjugate is N-palmitoyl D-erythro sphingosyl-1-carbamoyl spermine (CCS).

20. The method of claim 1, wherein said sphingoid-polyalkylamine conjugate associated with the nucleic acid molecule is also associated with a targeting substance.

* * * * *

UNITED STATES PATENT AND TRADEMARK OFFICE
CERTIFICATE OF CORRECTION

| | | |
|---|---|---|
| PATENT NO. | : 8,242,089 B2 | Page 1 of 1 |
| APPLICATION NO. | : 10/560932 | |
| DATED | : August 14, 2012 | |
| INVENTOR(S) | : Yechezkel Barenholz et al. | |

It is certified that error appears in the above-identified patent and that said Letters Patent is hereby corrected as shown below:

Title Page, Item (73) Assignee, after the first listed assignee "Yissum Research Development Company of the Hebrew University of Jerusalem, Jerusalem (IL)", insert the second assignee name as follows: --Biolab, Ltd., Jerusalem (IL)--.

Signed and Sealed this
Sixteenth Day of October, 2012

David J. Kappos
*Director of the United States Patent and Trademark Office*